(12) United States Patent
Gritzky et al.

(10) Patent No.: US 10,492,761 B2
(45) Date of Patent: Dec. 3, 2019

(54) UTILIZING DEPTH FROM ULTRASOUND VOLUME RENDERING FOR 3D PRINTING

(71) Applicant: General Electric Company, Schenectady, NY (US)

(72) Inventors: Arthur Gritzky, Oberösterreich (AT); Gerald Schroecker, Oberösterreich (AT)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 648 days.

(21) Appl. No.: 14/882,979

(22) Filed: Oct. 14, 2015

(65) Prior Publication Data
US 2017/0106597 A1    Apr. 20, 2017

(51) Int. Cl.
| | |
|---|---|
| A61B 8/00 | (2006.01) |
| A61B 8/08 | (2006.01) |
| G06T 19/00 | (2011.01) |
| G06T 15/00 | (2011.01) |
| B33Y 50/00 | (2015.01) |
| G06T 19/20 | (2011.01) |

(Continued)

(52) U.S. Cl.
CPC ............ A61B 8/461 (2013.01); A61B 8/0866 (2013.01); A61B 8/483 (2013.01); B33Y 50/00 (2014.12); *G06F 17/50* (2013.01); *G06K 15/02* (2013.01); *G06T 15/00* (2013.01); *G06T 17/00* (2013.01); *G06T 17/30* (2013.01); *G06T 19/00* (2013.01); *G06T 19/20* (2013.01); *G06T 2200/04* (2013.01); *G06T 2200/08* (2013.01)

(58) Field of Classification Search
CPC ... B29C 67/0088; B29C 67/00; A61B 8/0866; A61B 8/461; A61B 8/00; A61B 8/08; B33Y 10/00; B33Y 30/00; B33Y 50/02

USPC ............ 600/427; 382/154, 128, 131; 52/235
See application file for complete search history.

(56) References Cited

U.S. PATENT DOCUMENTS

| 8,646,229 B2 | 2/2014 | Grunewald et al. |
| 2003/0052875 A1* | 3/2003 | Salomie .................. G06T 17/20 345/419 |

(Continued)

OTHER PUBLICATIONS

"It Is Now Possible to 3D Print Your Unborn Fetus", by Mark Wilson, fastcodesign.com, dated Jan. 17, 2014, 3 pages.

(Continued)

*Primary Examiner* — Joel Lamprecht
(74) *Attorney, Agent, or Firm* — McAndrews, Held & Malloy, Ltd.; Jacob Groethe; David Bates

(57) ABSTRACT

Various embodiments include systems and methods for utilizing depth from ultrasound volume rendering for 3D printing. Volumetric ultrasound dataset may be generated, based on echo ultrasound signals, and one or more volume rendered ultrasound images, based on the volumetric ultrasound dataset, may be displayed. Based on the one or more volume rendered ultrasound images and/or the volumetric ultrasound dataset, three-dimensional (3D) printing data may be generated. The 3D printing data may be configured to enable producing, via a 3D printer, a physical volume representation of one or more objects and/or structures in the one or more volume rendered ultrasound images. The 3D printing data may be based on 3D modeling of at least a portion of at least one of the one or more volume rendered ultrasound images. The 3D modeling may comprise a surface mesh representation.

26 Claims, 6 Drawing Sheets

(51) Int. Cl.
G06F 17/50 (2006.01)
G06K 15/02 (2006.01)
G06T 17/30 (2006.01)
G06T 17/00 (2006.01)

(56) References Cited

U.S. PATENT DOCUMENTS

| | | |
|---|---|---|
| 2009/0316966 A1 | 12/2009 | Marshall et al. |
| 2012/0224755 A1* | 9/2012 | Wu .................. G06T 17/00 382/131 |
| 2015/0045662 A1 | 2/2015 | Kim et al. |
| 2015/0228070 A1 | 8/2015 | Birkbeck et al. |
| 2017/0085867 A1 | 3/2017 | Baran et al. |
| 2017/0109925 A1 | 4/2017 | Gritzky et al. |
| 2017/0347120 A1 | 11/2017 | Chou et al. |
| 2017/0357406 A1 | 12/2017 | Yi et al. |

OTHER PUBLICATIONS

"3D Printing Helps Expectant Parents Meet Their Baby Before it's Born", by Scott Grunewald, 3D Printing, Business, Medical 3D Printing, 3dprint.com, dated Aug. 5, 2015, 4 pages.

* cited by examiner

US 10,492,761 B2

UTILIZING DEPTH FROM ULTRASOUND VOLUME RENDERING FOR 3D PRINTING

CLAIMS OF PRIORITY

[Not Applicable]

CROSS-REFERENCE TO RELATED APPLICATIONS/INCORPORATION BY REFERENCE

[Not Applicable]

FIELD OF THE INVENTION

Certain embodiments of the invention relate to ultrasound imaging. More specifically, certain embodiments of the invention relate to methods and systems for utilizing depth from ultrasound volume rendering for three-dimensional (3D) printing.

BACKGROUND OF THE INVENTION

Ultrasound imaging is a medical imaging technique for imaging organs and soft tissues in a human body. Ultrasound imaging uses real time, non-invasive high frequency sound waves to produce ultrasound images. These ultrasound images may be two-dimensional (2D), three-dimensional (3D), and/or four-dimensional (4D) images (which may essentially be real-time/continuous 3D images).

With 3D (and similarly 4D) images, volumetric ultrasound datasets may be acquired and used in rendering the ultrasound images (e.g., via a display). In some instances, it may be desirable to print copies of the ultrasound images. For example, parents may want printouts of ultrasound images displayed during obstetric (OB) ultrasound imaging. Typically ultrasound images (regardless of whether they are 2D or 3D/4D) are only printed 2D (e.g. on flat sheets).

Further limitations and disadvantages of conventional and traditional approaches will become apparent to one of skill in the art, through comparison of such systems with some aspects of the present invention as set forth in the remainder of the present application with reference to the drawings.

BRIEF SUMMARY OF THE INVENTION

A system and/or method is provided for utilizing depth from ultrasound volume rendering for 3D printing, substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

DETAILED DESCRIPTION OF THE INVENTION

Figure 1:
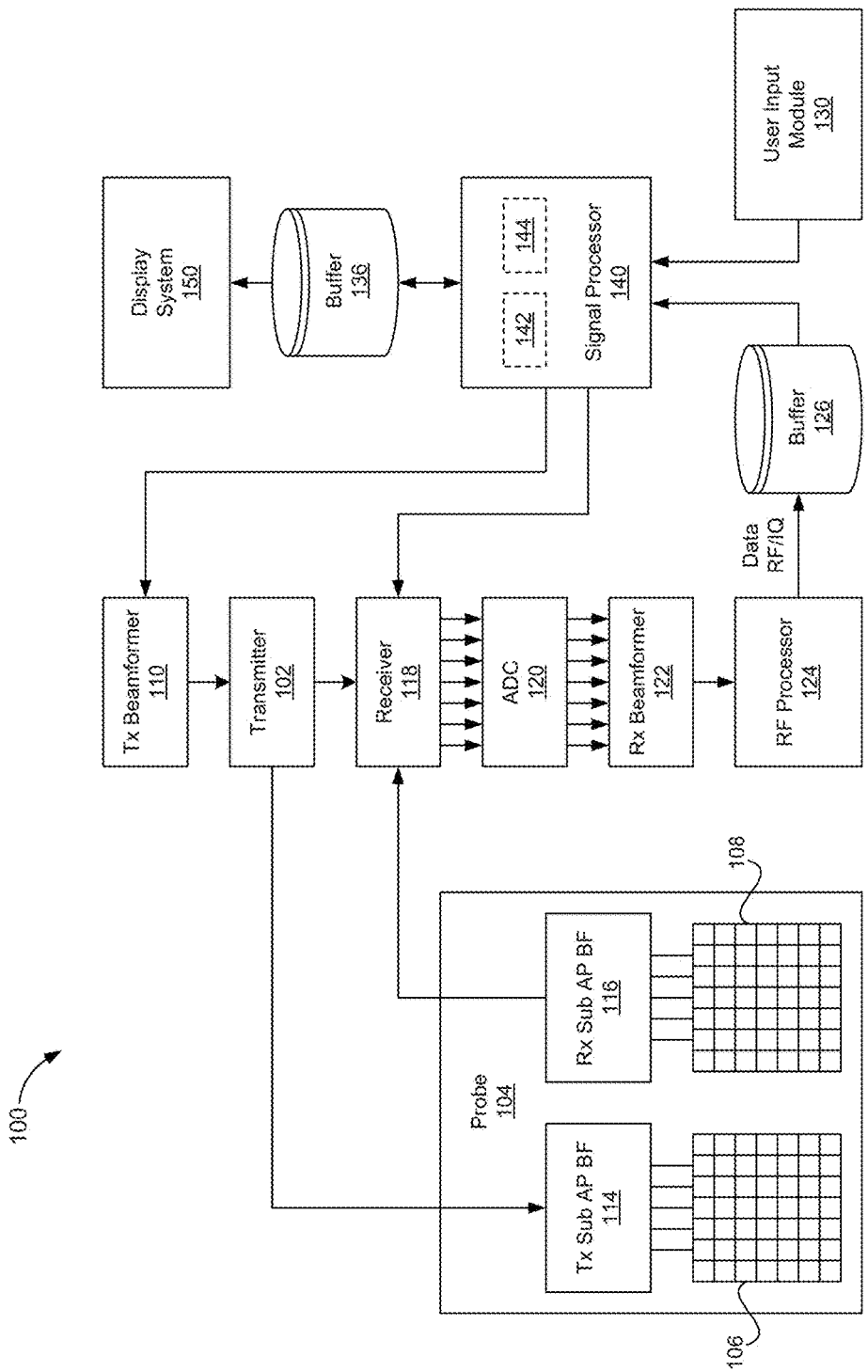
FIG. 1 is a block diagram illustrating an example ultrasound system that may be used in ultrasound imaging, which may support three-dimensional (3D) printing, in accordance with various embodiments of the invention.

Certain embodiments of the invention may be found in methods and systems for utilizing depth from ultrasound volume rendering for three-dimensional (3D) printing. For example, aspects of the present invention have the technical effect of facilitating 3D printing during ultrasound imaging by generating 3D printing data based on the volume rendered ultrasound images. In this regard, volumetric ultrasound dataset may be generated, such as based on echo ultrasound signals, volume rendered ultrasound images may be generated and/or displayed, based on the volumetric ultrasound dataset. The 3D printing data may then be generated, based on the volume rendered ultrasound images and/or the volumetric ultrasound dataset, with the 3D printing data being configured to enable producing, via a 3D printer, a physical volume representation of one or more objects and/or structures in the volume rendered ultrasound images. The 3D printing data may be based on 3D modeling of at least a portion of at least one volume rendered ultrasound image. The 3D modeling may comprise a surface mesh representation (e.g., 2D or 3D) of the volume rendered ultrasound image, or the at least portion thereof.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments of the present invention. The following detailed description is, therefore, not to be taken in a limiting sense, and the scope of the present invention is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an embodiment," "one embodiment," "a representative embodiment," "an example embodiment," "various embodiments," "certain embodiments," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

In addition, as used herein, the phrase "pixel" also includes embodiments of the present invention where the data is represented by a "voxel." Thus, both the terms "pixel" and "voxel" may be used interchangeably throughout this document.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode, CF-mode and/or sub-modes of CF such as TVI, Angio, B-flow, BMI, BMI_Angio, and in some cases also MM, CM, PW, TVD, CW where the "image" and/or "plane" includes a single beam or multiple beams.

Furthermore, the term processor or processing unit, as used herein, refers to any type of processing unit that can carry out the required calculations needed for the invention, such as single or multi-core: CPU, Graphics Board, DSP, FPGA, ASIC, or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams." Also, forming of images may be performed using channel combinations that may originate from more than one transmit event (e.g., synthetic aperture techniques).

In various embodiments, ultrasound processing, including visualization enhancement, to form images may be performed, for example, in software, firmware, hardware, or a combination thereof. One implementation of an ultrasound system in accordance with various embodiments is illustrated in FIG. 1.

FIG. 1 is a block diagram illustrating an example ultrasound system that may be used in ultrasound imaging, which may support three-dimensional (3D) printing, in accordance with various embodiments of the invention.

FIG. 1 is a block diagram illustrating an example ultrasound system that may be used in ultrasound imaging, which may support amniotic fluid position detection based on shear wave propagation, in accordance with various embodiments of the invention. Shown in FIG. 1 is an ultrasound system 100.

The ultrasound system 100 comprises, for example, a transmitter 102, an ultrasound probe 104, a transmit beamformer 110, a receiver 118, a receive beamformer 122, a RF processor 124, a RF/IQ buffer 126, a user input module 130, a signal processor 140, an image buffer 136, and a display system 150.

The transmitter 102 may comprise suitable circuitry that may be operable to drive an ultrasound probe 104. The transmitter 102 and the ultrasound probe 104 may be implemented and/or configured for one-dimensional (1D), two-dimensional (2D), three-dimensional (3D), and/or four-dimensional (4D) ultrasound scanning. In this regard, ultrasound probe 104 may comprise a one-dimensional (1D, 1.25D, 1.5D or 1.75D) array or a two-dimensional (2D) array of piezoelectric elements. For example, as shown in FIG. 1, the ultrasound probe 104 may comprise a group of transmit transducer elements 106 and a group of receive transducer elements 108, that normally constitute the same elements. The transmitter 102 may be driven by the transmit beamformer 110.

The transmit beamformer 110 may comprise suitable circuitry that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). In this regard, the group of transmit transducer elements 106 can be activated to transmit ultrasonic signals. The ultrasonic signals may comprise, for example, pulse sequences that are fired repeatedly at a pulse repetition frequency (PRF), which may typically be in the kilohertz range. The pulse sequences may be focused at the same transmit focal position with the same transmit characteristics. A series of transmit firings focused at the same transmit focal position may be referred to as a "packet."

The transmitted ultrasonic signals may be back-scattered from structures in the object of interest, like tissue, to produce echoes. The echoes are received by the receive transducer elements 108. The group of receive transducer elements 108 in the ultrasound probe 104 may be operable to convert the received echoes into analog signals, undergo sub-aperture beamforming by a receive sub-aperture beamformer 116 and are then communicated to the receiver 118.

The receiver 118 may comprise suitable circuitry that may be operable to receive and demodulate the signals from the probe transducer elements or receive sub-aperture beamformer 116. The demodulated analog signals may be communicated to one or more of the plurality of A/D converters (ADCs) 120.

Each plurality of A/D converters 120 may comprise suitable circuitry that may be operable to convert analog signals to corresponding digital signals. In this regard, the plurality of A/D converters 120 may be configured to convert demodulated analog signals from the receiver 118 to corresponding digital signals. The plurality of A/D converters 120 are disposed between the receiver 118 and the receive beamformer 122. Notwithstanding, the invention is not limited in this regard. Accordingly, in some embodiments of the invention, the plurality of A/D converters 120 may be integrated within the receiver 118.

The receive beamformer 122 may comprise suitable circuitry that may be operable to perform digital beamforming processing to, for example, sum the delayed channel signals received from the plurality of A/D converters 120 and output a beam summed signal. The resulting processed information may be converted back to corresponding RF signals. The corresponding output RF signals that are output from the receive beamformer 122 may be communicated to the RF processor 124. In accordance with some embodiments of the invention, the receiver 118, the plurality of A/D converters 120, and the beamformer 122 may be integrated into a single beamformer, which may be digital.

The RF processor 124 may comprise suitable circuitry that may be operable to demodulate the RF signals. In some instances, the RF processor 124 may comprise a complex demodulator (not shown) that is operable to demodulate the RF signals to form In-phase and quadrature (IQ) data pairs (e.g., B-mode data pairs) which may be representative of the corresponding echo signals. The RF (or IQ) signal data may then be communicated to an RF/IQ buffer 126.

The RF/IQ buffer 126 may comprise suitable circuitry that may be operable to provide temporary storage of output of the RF processor 124—e.g., the RF (or IQ) signal data, which is generated by the RF processor 124.

The user input module 130 may comprise suitable circuitry that may be operable to enable obtaining or providing input to the ultrasound system 100, for use in operations thereof. For example, the user input module 130 may be used to input patient data, surgical instrument data, scan parameters, settings, configuration parameters, change scan mode, and the like. In an example embodiment of the invention, the user input module 130 may be operable to configure, manage and/or control operation of one or more components and/or modules in the ultrasound system 100. In this regard, the user input module 130 may be operable to configure, manage and/or control operation of transmitter 102, the ultrasound probe 104, the transmit beamformer 110, the receiver 118, the receive beamformer 122, the RF processor 124, the RF/IQ buffer 126, the user input module 130, the signal processor 140, the image buffer 136, and/or the display system 150.

The signal processor 140 may comprise suitable circuitry that may be operable to process the ultrasound scan data (e.g., the RF and/or IQ signal data) and/or to generate corresponding ultrasound images, such as for presentation on the display system 150. The signal processor 140 is operable to perform one or more processing operations according to a plurality of selectable ultrasound modalities on the acquired ultrasound scan data. In some instances, the signal processor 140 may be operable to perform compounding, motion tracking, and/or speckle tracking. Acquired ultrasound scan data may be processed in real-time—e.g., during a B-mode scanning session, as the B-mode echo signals are received. Additionally or alternatively, the ultrasound scan data may be stored temporarily in the RF/IQ buffer 126 during a scanning session and processed in less than real-time in a live or off-line operation.

In operation, the ultrasound system 100 may be used in generating ultrasonic images, including two-dimensional (2D), three-dimensional (3D), and/or four-dimensional (4D) images. In this regard, the ultrasound system 100 may be operable to continuously acquire ultrasound scan data at a particular frame rate, which may be suitable for the imaging situation in question. For example, frame rates may range from 20-70 but may be lower or higher. The acquired ultrasound scan data may be displayed on the display system 150 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several seconds' worth of frames of ultrasound scan data. The frames of ultrasound scan data are stored in a manner to facilitate retrieval thereof according to its order or time of acquisition. The image buffer 136 may be embodied as any known data storage medium.

In some instances, the ultrasound system 100 may be configured to support grayscale and color based operations. For example, the signal processor 140 may be operable to perform grayscale B-mode processing and/or color processing. The grayscale B-mode processing may comprise processing B-mode RF signal data or IQ data pairs. For example, the grayscale B-mode processing may enable forming an envelope of the beam-summed receive signal by computing the quantity $(I^2+Q^2)^{1/2}$. The envelope can undergo additional B-mode processing, such as logarithmic compression to form the display data. The display data may be converted to X-Y format for video display. The scan-converted frames can be mapped to grayscale for display.

The B-mode frames that are provided to the image buffer 136 and/or the display system 150. The color processing may comprise processing color based RF signal data or IQ data pairs to form frames to overlay on B-mode frames that are provided to the image buffer 136 and/or the display system 150. The grayscale and/or color processing may be adaptively adjusted based on user input—e.g., a selection from the user input module 130, for example, for enhance of grayscale and/or color of particular area.

In some instances, ultrasound imaging may include generation and/or display of volumetric ultrasound images—that is where objects (e.g., organs, tissues, etc.) are displayed three-dimensional 3D. In this regard, with 3D (and similarly 4D) imaging, volumetric ultrasound datasets may be acquired, comprising voxels that correspond to the imaged objects. This may be done, e.g., by transmitting the sound waves at different angles rather than simply transmitting them in one direction (e.g., straight down), and then capture their reflections back. The returning echoes (of transmissions at different angles) are then captured, and processed (e.g., via the signal processor 140) to generate the corresponding volumetric datasets, which may in turn be used (e.g., via a 3D rendering module 142 in the signal processor 140) in creating and/or displaying volume (e.g. 3D) images, such as via the display 150. This may entail use of particular handling techniques to provide the desired 3D perception. For example, volume rendering techniques may be used in displaying projections (e.g., 2D projections) of the volumetric (e.g., 3D) datasets. In this regard, rendering a 2D projection of a 3D dataset may comprise setting or defining a perception angle in space relative to the object being displayed, and then defining or computing necessary information (e.g., opacity and color) for every voxel in the dataset. This may be done, for example, using suitable transfer functions for defining RGBA (red, green, blue, and alpha) value for every voxel.

In some instances, it may be desirable to print copies of the ultrasound images. For example, parent(s) may want to have printout of the ultrasound images displayed during obstetric (OB) ultrasound imaging. Typically copies of the ultrasound images (regardless of whether they are 2D or 3D/4D) are only printed two-dimensionally (e.g., as 2D black-and-white or colored sheets). However, 3D printing is also becoming popular. In 3D printing, three-dimensional (volume) physical objects may be synthesized, using suitable 3D printers. In this regard, 3D printers may, for example, utilize additive processes to lay successive layers of material. The synthesized volume objects may be of almost any shape and/or geometry. The 3D printers and/or operations thereof (during 3D printing) may be configured and/or controlled based on data (referred to hereafter as "3D printing data"), which may be generated and/or formatted in accordance with one or more defined formats for use in 3D printing, such as STL (STereoLithography) file format based data. In this regard, the 3D printing data may comprise information corresponding to and/or representing the would-be printed objects (or structures thereof). For example, the 3D printing data may comprise and/or be based on 3D modeling (or information relating thereto) of the would-be printed objects.

Accordingly, in various embodiments in accordance with the present disclosure, ultrasound imaging may support 3D printing. This may be done by, for example, utilizing volumetric ultrasound datasets (e.g., via a 3D printing module 144 in the signal processor 140) to generate and/or configure 3D printing data, which may be provided to 3D printers to perform the 3D printing. An example ultrasound imaging setup that may be used in supporting 3D printing is depicted in FIG. 2.

Some challenges may exist when generating such 3D printing data, however. For example, quality of the 3D printing may (e.g., due to quality and/or accuracy of the 3D printing data) depend on and/or be adversely affected by characteristics of the ultrasound imaging, such as bad signal quality (e.g., due to noise, speckle, acoustic shadowing, etc.), difficult tissue differentiation with no defined gray values to distinguish anatomical objects, etc. Thus, the generation of 3D printing data (e.g., via the 3D printing module 144) based on the ultrasound imaging and/or the volumetric ultrasound datasets acquired during such imaging may be configured and/or adjusted to optimize the quality of 3D printing, such as by adaptively configuring and/or controlling the generation of the 3D printing data, to account for such issues and/or defects for example.

In some example embodiments, the 3D printing data may be generated based on surface mesh representation (e.g., polygon mesh) suitable for 3D printing. A polygon mesh may be a collection of vertices, edges, and/or polygons faces (e.g., triangles, quadrilaterals, etc.) for defining the shape of an object in a polyhedral manner, to facilitate 3D modeling of that object. Such surface mesh representations may be obtained by, for example, converting 3D scalar volume data. For example, depth information may be extracted (e.g., via the 3D rendering module 142) based on volumetric ultrasound datasets and/or volume rendering, and this depth information may then be used (e.g., via the 3D printing module 144) in creating a relief like mesh. The surface mesh representation may be a 2D mesh. In certain example embodiments, however, 3D mesh representations may be created. For example, two or more volume renderings, such as from different viewing directions, may be used to create not only a relief mesh but a full 3D mesh.

Figure 2:
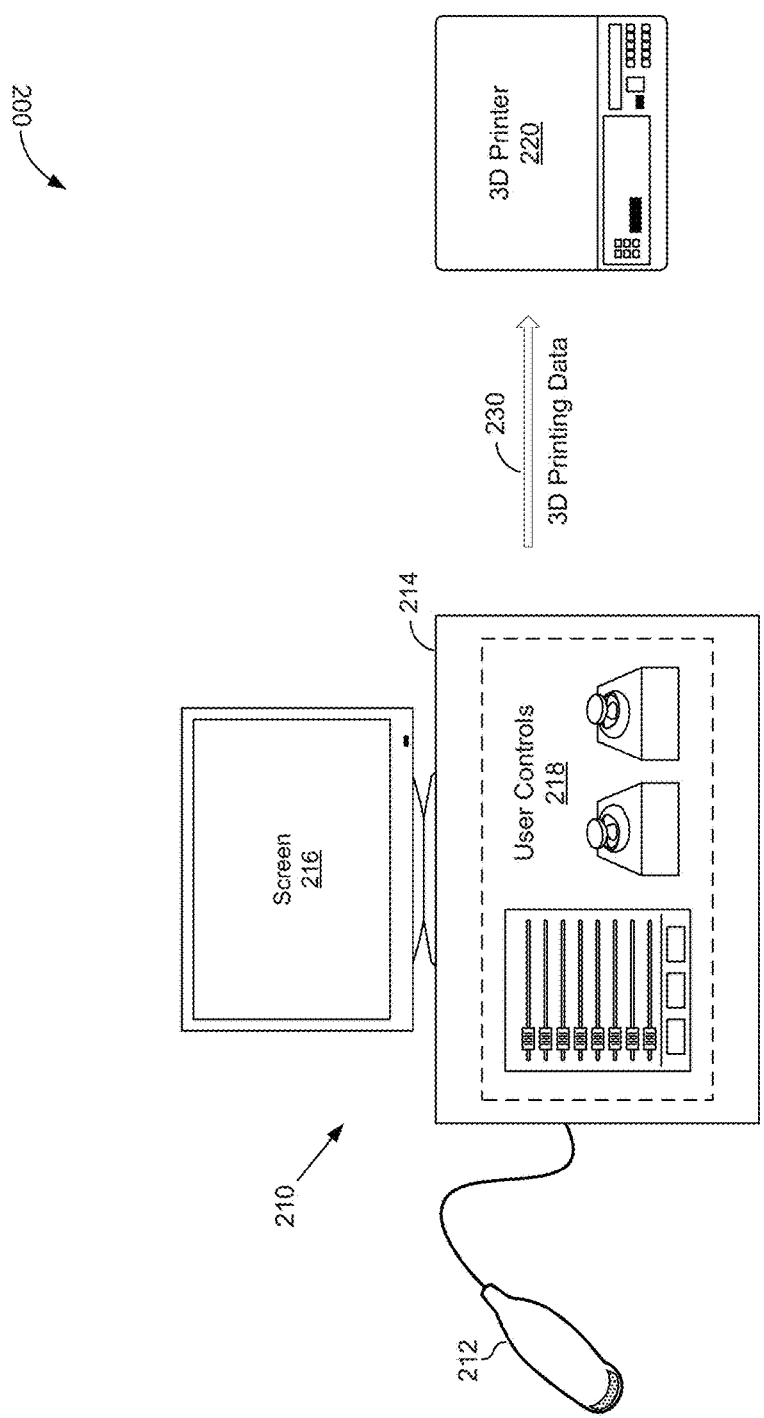
FIG. 2 is a block diagram illustrating an example use of ultrasound system during three-dimensional (3D) printing, in accordance with an example embodiment of the invention.

FIG. 2 is a block diagram illustrating an example use of ultrasound system during three-dimensional (3D) printing, in accordance with an example embodiment of the invention. Shown in FIG. 2 is a setup 200, comprising an ultrasound system 210 and a 3D printer 220.

The ultrasound system 210 may be substantially similar to the ultrasound system 100, and as such may comprise generally similar components as described with respect to the ultrasound system 100 of FIG. 1. As shown in FIG. 2, the ultrasound system 210 may comprise a portable and movable ultrasound probe 212 and a display/control unit 212. The ultrasound probe 212 may be used in generating and/or capturing ultrasound images (or data corresponding thereto), such as by being moved over a patient's body (or part thereof). The display/control unit 212 may be used in displaying ultrasound images (e.g., via a screen 216). Further, the display/control unit 212 may support user interactions (e.g., via user controls 218), such as to allow controlling of the ultrasound imaging. The user interactions may comprise user input or commands controlling display of ultrasound images, selecting settings, specifying user preferences, providing feedback as to quality of imaging, etc.

The 3D printer 220 may be operable to perform 3D printing. In this regard, the 3D printer 220 may be configured to produce (e.g., synthesize) three-dimensional physical representations, such as based on the 3D printing data corresponding to and/or based on 3D model of the would-be printed objects. The 3D printer 220 may be any of commercially available products, which may be communicatively coupled to the ultrasound system 210, via suitable connections, wired (e.g., cords) and/or wireless (e.g., WiFi, Bluetooth, etc.). The 3D printer 220 may also be part of the ultrasound system 210 itself, and may even by incorporated directly into it.

In operation, the ultrasound system 210 may be used in ultrasound imaging, such as to generate and present (e.g., display) ultrasound images, including 2D, 3D, and/or 4D ultrasound images, and/or to support user input in conjunction therewith, substantially as described with respect to FIG. 1. Further, however, the ultrasound system 210 may be operable to support 3D printing via the 3D printer 220, substantially as described with respect to FIG. 1. The 3D printing may correspond to printing volume (3D) representations of objects and/or structures in displayed ultrasound images. For example, this may be done by utilizing volumetric ultrasound datasets acquired and/or generated in the ultrasound system 210 to generate and/or configure 3D printing data 230, which may be provided (e.g., communicated, such as via wired and/or wireless connections) to the 3D printer 220. In this regard, the 3D printing may be configured based on 3D modelling of the objects and/or structures in the ultrasound images, and/or may be particularly formatted based on the supported printing data formats in the 3D printer 220. Further, the generation of the 3D printing data 230 may be adaptively configured and/or controlled, to account for and/or mitigate possible issues and/or defects relating to the ultrasound imaging and/or data corresponding thereto.

In an example implementation, the ultrasound system 210 may be operable to generate the 3D printing data 230 based on surface mesh representation, such as a 2D or 3D polygon (e.g., triangle) mesh, which may be generated based on the volumetric ultrasound datasets acquired via the ultrasound system 210 and/or volume rendering based thereon. In an example use scenario, a direct volume rendering may be used in generating 2D image from a volumetric ultrasound dataset. For example, in instances where ultrasound imaging is configured based on the RGB color model (to provide colored ultrasound images), in addition to the RGB color information forming the 2D image, a depth value is computed for every pixel. The depth information may then be used in creating a relief-like mesh (e.g., polygon mesh), where the depth values are used as the height for a regular grid of vertices which are connect by polygons (e.g., triangles) to form a closed mesh. The depth value may be the centroid of the opacity increase for each ray along depth. An example of generation of a mesh representation based on volume datasets and/or volume rendering during ultrasound imaging is illustrated in more detail with respect to FIGS. 3A-3C, below.

Providing 3D printing in this manner—that is based on and/or in conjunction with ultrasound imaging—is be advantageous. This approach would ensure that 3D prints (objects) would look exactly as the rendering on the screen 216. Also, a fully automated workflow from volume data to 3D printing is possible with this approach, allowing for efficient and/or easy-to-use operation. Further, the rendering operations may enhance the quality of the 3D printing—e.g., the rendering algorithm may act as non-linear filter smoothing the data and producing very reliable depth information compared to other segmentation methods. The rendered image (which matches the mesh) may also be used in texturing (e.g., colorizing) the 3D prints, the enhance quality (e.g., realism) of printed objects. This approach may also allow for control of the 3D printing by the user, such as based on user input (provided via the user controls 218). For example, the 3D printing may be controlled by the user based on user input relating to the volume rendering (e.g., selection of viewpoint, scaling, threshold, etc.). Further, the 3D printing may reflect use of techniques available for volume rendering, such as to cut away unwanted parts of the volume (e.g., masking with MagiCut, Vocal, Threshold, etc.). In other words, the 3D prints may only include the wanted parts of the objects.

Figure 3A:
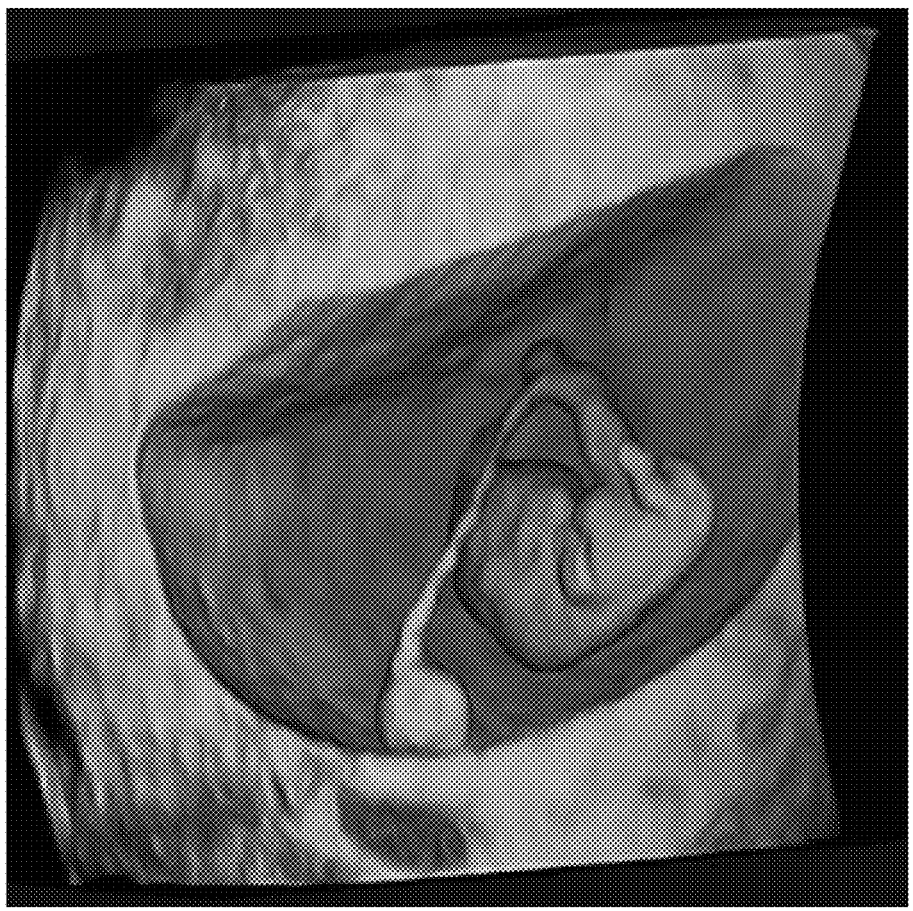
FIGS. 3A-3C illustrate example use of data corresponding to ultrasound volume rendering in generating polygon meshes for three-dimensional (3D) printing, in accordance with an example embodiment of the invention.
Figure 3B:
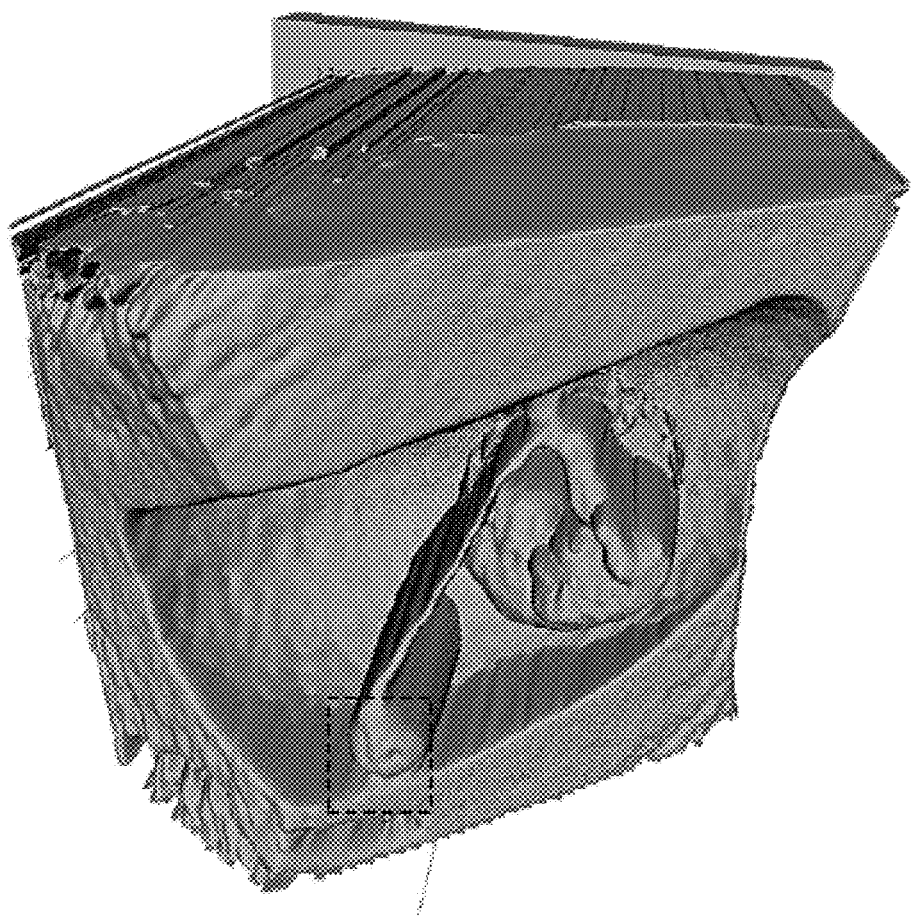
Figure 3C:
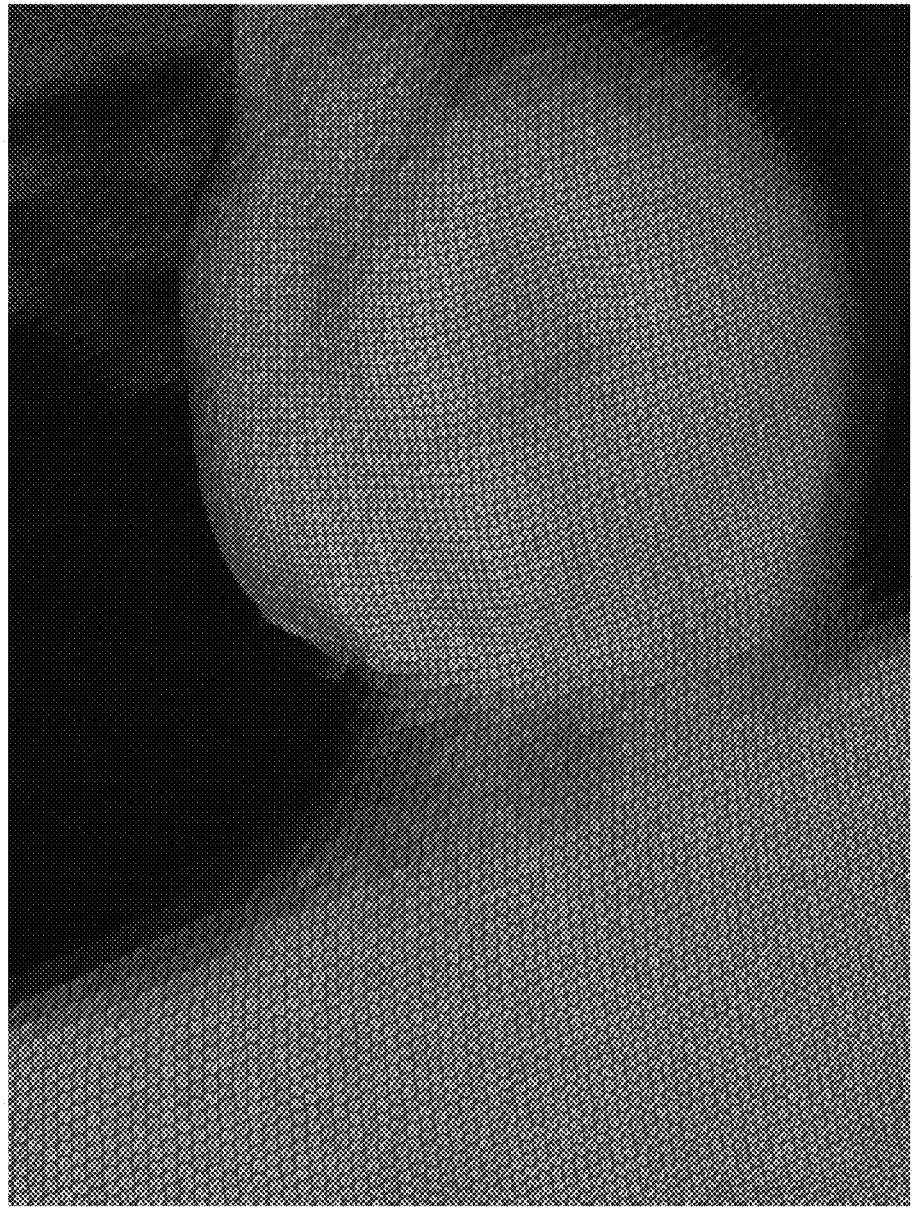

FIGS. 3A-3C illustrate example use of data corresponding to ultrasound volume rendering in generating polygon meshes for three-dimensional (3D) printing, in accordance with an example embodiment of the invention.

Shown in FIG. 3A is a volume rendered image 410, with depth. The image 410 may be rendered using volumetric ultrasound datasets, which may be acquired via an ultrasound system, such as the ultrasound system 210 of FIG. 2. The volumetric ultrasound datasets may comprise data (e.g., relating to ultrasound echoes) obtained from one or more angles or directions. Once acquired, the volumetric ultrasound datasets may be processed for volume (3D) rendering, such as via the 3D rendering module 142 of the signal processor 140. The volume rendering may comprise generating a projection (e.g., 2D projection) that provides the desired 3D perception. Processing relating to the volume rendering may comprise, for example, determining depth information (e.g., for each voxel), and using that depth information in the 2D projection.

Shown in FIG. 3B is an example mesh 420, which may be generated (e.g., from a slightly different angle) based on the volume rendered image 410 or volumetric dataset corresponding thereto, substantially as described above. In this regard, the mesh 420 may be created using depth values computed for the volume rendered image 410 (e.g., from the volumetric dataset, for every voxel), based on the defined angle for the mesh 420, such as by applying the depth values as the height for each regular grid of vertices which are connect by polygons (e.g., triangles) to form the mesh 410. Details of an example mesh are shown in FIG. 3C, which depicts a zoomed-in section in the mesh 420 (shown as a dashed box in FIG. 3B) to illustrated polygons in the mesh.

Figure 4:
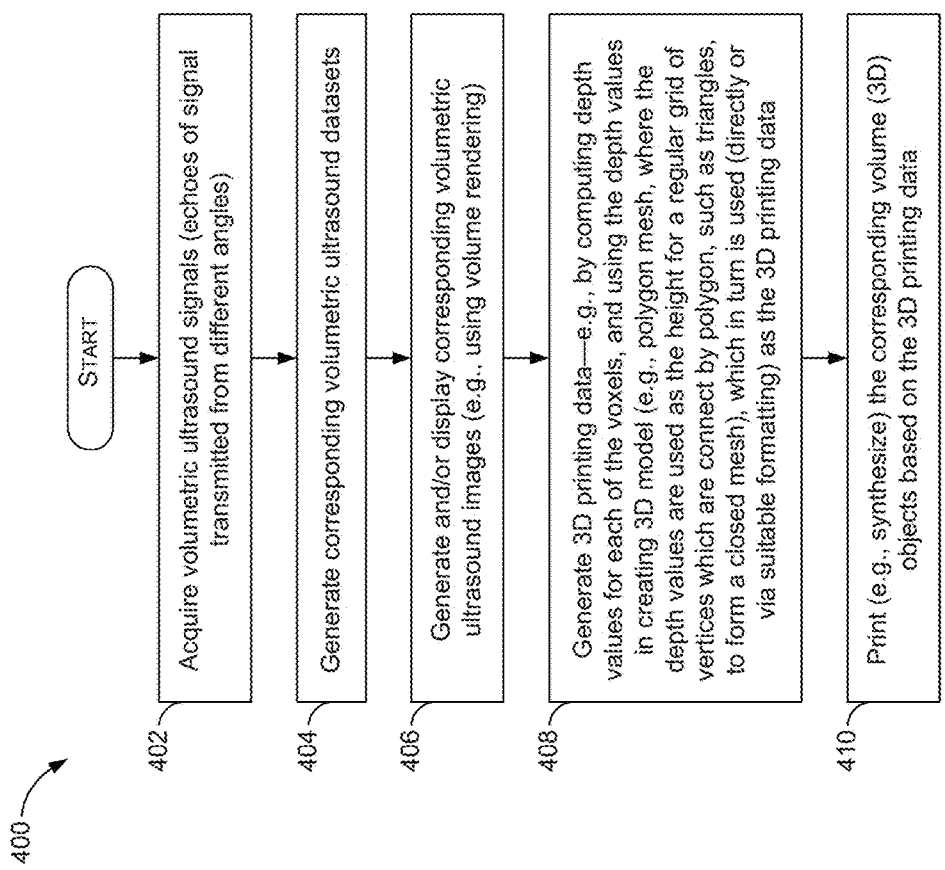
FIG. 4 is a flow chart illustrating example steps that may be performed for utilizing data from ultrasound volume rendering for three-dimensional (3D) printing, in accordance with an embodiment of the invention.

FIG. 4 is a flow chart illustrating example steps that may be performed for utilizing data from ultrasound volume rendering for three-dimensional (3D) printing, in accordance with an embodiment of the invention. Shown in FIG. 4 is a flow chart 400, which comprises a plurality of example steps, corresponding to an example method.

The technical effect of the method corresponding to flow chart 400 is supporting three-dimensional (3D) printing (e.g., by generating data or files based thereon using the in 3D printers) based on the data acquired and/or generated for ultrasound volume rendering in an ultrasound system (e.g., the ultrasound system 100). For example, the example steps of the method corresponding to flow chart 400 may be executed and/or performed by the various components of the ultrasound system 100.

It should be understood, however, that certain embodiments of the present invention may omit one or more of the steps, and/or perform the steps in a different order than the order listed, and/or combine certain of the steps discussed below. For example, some steps may not be performed in certain embodiments of the present invention. As a further example, certain steps may be performed in a different temporal order, including simultaneously, than listed below.

In step 402, after a start step (in which an ultrasound system may be, for example, initialized and/or configured for ultrasound imaging), volumetric ultrasound signals (echoes of signal transmitted from different angles) may be acquired.

In step 404, corresponding volumetric ultrasound datasets may be generated based on the acquired ultrasound images.

In step 406, corresponding volumetric ultrasound images may be generated and/or displayed (e.g., using volume rendering).

In step 408, 3D printing data may be generated. This may be done, as described above with respect to FIG. 2 for example, by computing depth values for each of the voxels, and using the depth values in creating 3D model (e.g., polygon mesh, where the depth values are used as the height for a regular grid of vertices which are connect by polygon, such as triangles, to form a closed mesh), which in turn may be used (directly or via suitable formatting) as the 3D printing data.

In step 410, the corresponding volume (3D) objects may be printed (e.g., synthesized) based on the 3D printing data.

As utilized herein the term "circuitry" refers to physical electronic components (e.g., hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or." As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "example" means serving as a non-limiting example, instance, or illustration. As utilized herein, the terms "for example" and "e.g.," set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments of the invention may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for utilizing depth from ultrasound volume rendering for three-dimensional (3D) printing.

Accordingly, the present invention may be realized in hardware, software, or a combination of hardware and software. The present invention may be realized in a centralized fashion in at least one computer system, or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

The present invention may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A system, comprising:
    an ultrasound device, comprising at least one processor, wherein the ultrasound device:
        generates volumetric ultrasound dataset, based on echo ultrasound signals;
        generates based on the volumetric ultrasound dataset, a two-dimensional (2D) surface representation, wherein:
            each point in the 2D surface representation has a corresponding height value; and
            each height value is adaptively weighted based on measurements corresponding to multiple voxels along a ray intersecting the 2D surface representation; and
        generates, based on the 2D surface representation, three-dimensional (3D) printing data;
        wherein the 3D printing data is configured to enable producing, via a printer, a physical volume representation of one or more objects and/or structures in ultrasound images rendered based on the volumetric ultrasound dataset.

2. The system of claim 1, wherein the ultrasound device:
    generates 3D modeling of at least a portion of the one or more objects and/or structures; and
    generates the 3D printing data based on the 3D modeling.

3. The system of claim 1, wherein the ultrasound device:
    generates a mesh representation of at least a portion of the one or more objects and/or structures; and
    generates the 3D printing data based on the mesh representation.

4. The system of claim 3, wherein the ultrasound device, when generating the mesh representation:
    computes one or more depth values, each associated with one voxel, corresponding to at least the portion of the one or more objects and/or structures; and
    applies the computed one or more depth values as height to a grid of plurality of vertices connected by a plurality of polygons.

5. The system of claim 1, wherein the ultrasound device:
    receives user input; and
    adaptively controls generating the 3D printing data in response to the user input.

6. The system of claim 1, wherein the ultrasound device configures and/or formats the 3D printing data based on a pre-defined 3D printing standard or file format.

7. The system of claim 1, wherein the ultrasound device: computes based on the depth information, one or more depth values for each voxel corresponding to at least a portion of at least the one of the one or more volume rendered ultrasound images; and
    generates the three-dimensional (3D) printing data based on said depth values.

8. The system of claim 1, wherein the ultrasound device generates adaptive weight for each height value in the 2D surface representation based on opacity based measurements corresponding to the multiple voxels.

9. A method, comprising:
    capturing echo ultrasound signals;
    generating volumetric ultrasound dataset, based on echo ultrasound signals;
    generating based on the volumetric ultrasound dataset, a two-dimensional (2D) surface representation, wherein:
        each point in the 2D surface representation has a corresponding height value; and
        each height value is adaptively weighted based on measurements corresponding to multiple voxels along a ray intersecting the 2D surface representation; and
    generating, based on the 2D surface representation, three-dimensional (3D) printing data;
    wherein the 3D printing data is configured to enable producing, via a printer, a physical volume representation of one or more objects and/or structures in ultrasound images rendered based on the volumetric ultrasound dataset.

10. The method of claim 9, comprising:
    generating 3D modeling of at least a portion of the one or more objects and/or structures; and
    generating the 3D printing data based on the 3D modeling.

11. The method of claim 9, comprising:
    generating mesh representation of at least a portion the one or more objects and/or structures; and
    generating the 3D printing data based on the mesh representation.

12. The method of claim 11, comprising generating the mesh representation by:
    computing one or more depth values, each associated with one voxel, corresponding to at least the portion of the one or more objects and/or structures; and
    applying the computed one or more depth values as height to a grid of plurality of vertices connected by a plurality of polygons.

13. The method of claim 9, comprising:
    receiving user input; and
    adaptively controlling the generating of the 3D printing data in response to the user input.

14. The method of claim 13, wherein the user input is directed to parameters and/or characteristics of the volume rendering.

15. The method of claim 13, comprising configuring and/or formatting the 3D printing data based on a pre-defined 3D printing standard or file format.

16. The method of claim 9, comprising:
    computing based on the depth information, one or more depth values for each voxel corresponding to at least a portion of at least the one of the one or more volume rendered ultrasound images; and
    generating the three-dimensional (3D) printing data based on said depth values.

17. The method of claim 9, comprising generating adaptive weight for each height value in the 2D surface representation based on opacity based measurements corresponding to the multiple voxels.

18. A non-transitory computer readable medium having stored thereon, a computer program having at least one code section, the at least one code section being executable by a machine for causing the machine to perform one or more steps comprising:
- capturing echo ultrasound signals;
- generating volumetric ultrasound dataset, based on echo ultrasound signals;
- generating based on the volumetric ultrasound dataset, a two-dimensional (2D) surface representation, wherein:
  - each point in the 2D surface representation has a corresponding height value; and
  - each height value is adaptively weighted based on measurements corresponding to multiple voxels along a ray intersecting the 2D surface representation; and
- generating, based on the 2D surface representation, three-dimensional (3D) printing data;
- wherein the 3D printing data is configured to enable producing, via a printer, a physical volume representation of one or more objects and/or structures in ultrasound images rendered based on the volumetric ultrasound dataset.

19. The non-transitory computer readable medium of claim 18, the one or more steps further comprising:
- generating 3D modeling of at least a portion of the one or more objects and/or structures; and
- generating the 3D printing data based on the 3D modeling.

20. The non-transitory computer readable medium of claim 18, the one or more steps further comprising:
- generating a mesh representation of at least a portion the one or more objects and/or structures; and
- generating the 3D printing data based on the mesh representation.

21. The non-transitory computer readable medium of claim 20, the one or more steps further comprising:
- computing one or more depth values, each associated with one voxel, corresponding to at least the portion of the one or more objects and/or structures; and
- applying the computed one or more depth values as height to a grid of plurality of vertices connected by a plurality of polygons.

22. The non-transitory computer readable medium of claim 18, the one or more steps further comprising:
- receiving user input; and
- adaptively controlling the generating of the 3D printing data in response to the user input.

23. The non-transitory computer readable medium of claim 18, wherein the user input is directed to parameters and/or characteristics of the volume rendering.

24. The non-transitory computer readable medium of claim 18, the one or more steps further comprising configuring and/or formatting the 3D printing data based on a pre-defined 3D printing standard or file format.

25. The non-transitory computer readable medium of claim 18, the one or more steps further comprising:
- computing based on the depth information, one or more depth values for each voxel corresponding to at least a portion of at least the one of the one or more volume rendered ultrasound images; and
- generating the three-dimensional (3D) printing data based on said depth values.

26. The non-transitory computer readable medium of claim 18, the one or more steps further comprising generating adaptive weight for each height value in the 2D surface representation based on opacity based measurements corresponding to the multiple voxels.

* * * * *